United States Patent [19]

Kurosu et al.

[11] Patent Number: 4,696,947

[45] Date of Patent: Sep. 29, 1987

[54] NEMATOCIDE

[75] Inventors: Yasuhisa Kurosu; Hiroshi Kawada; Haruki Kanasugi; Akio Hosokawa, all of Tokyo, Japan

[73] Assignee: Hodogaya Chemical Co., Ltd., Tokyo, Japan

[21] Appl. No.: 462,964

[22] Filed: Feb. 1, 1983

Related U.S. Application Data

[63] Continuation of Ser. No. 300,618, Sep. 9, 1981, abandoned.

[30] Foreign Application Priority Data

Oct. 21, 1980 [JP]  Japan ................................ 55-146360
Oct. 21, 1980 [JP]  Japan ................................ 55-146361

[51] Int. Cl.$^4$ ...................... A01N 25/00; A01N 47/10
[52] U.S. Cl. .................................... 514/478; 514/770; 514/951
[58] Field of Search ................ 424/300; 514/478, 770, 514/951

[56] References Cited

U.S. PATENT DOCUMENTS

| | | | |
|---|---|---|---|
| 3,046,189 | 7/1962 | Jacobi et al. | 424/300 |
| 3,089,887 | 5/1963 | Metivier | 424/300 |
| 3,441,590 | 4/1969 | Ottmann et al. | 424/300 |
| 3,513,241 | 5/1970 | Hoyer et al. | 424/300 |
| 3,846,467 | 11/1974 | Kudamatsu et al. | 424/300 |
| 3,886,282 | 5/1975 | Brown | 424/300 |
| 4,281,016 | 7/1981 | Kurosu et al. | 424/300 |

FOREIGN PATENT DOCUMENTS

| | | |
|---|---|---|
| 862548 | 3/1961 | United Kingdom . |
| 862250 | 3/1961 | United Kingdom . |
| 868111 | 5/1961 | United Kingdom . |
| 882111 | 11/1961 | United Kingdom . |
| 882110 | 11/1961 | United Kingdom . |

*Primary Examiner*—Allen J. Robinson
*Attorney, Agent, or Firm*—Oblon, Fisher, Spivak, McClelland & Maier

[57] ABSTRACT

A nematocide comprises S-methyl-N,N-di-$C_{1-2}$ alkyl thiolcarbamate as an active ingredient.

7 Claims, No Drawings

NEMATOCIDE

This is a continuation of application Ser. No. 300,618, filed Sept. 9, 1981 and now abandoned.

BACKGROUND OF THE INVENTION

1. Field of the Invention

The present invention relates to a nematocide for controlling nematode in soil to prevent nematode.

2. Description of the Prior Art

It has been important to control soil pests, for perennial crops such as fruit trees and tea tree. Recently, a concentrated utilization of up-lands, a greenhouse culture and a special production of vegetables have been developed to cause an injury by continuous cropping caused by soil nematode and disease germs. In an upland which is not suitable for culturing crop plants, it has been known that soil nematode affect to the troubles.

The damages caused by the soil nematode are found in various forms and are usually a poor initial growth, a death and a reduction of yield caused by the poor growth or the death. In the case of a root crop plants, the soil nematode remarkably damage a market value of root crops by a deformation or a surface damage. Once, a damage caused by nematode is given in an up-land, it is impossible to attain a continuous cropping. It is not easy to consider a rotation cropping system under a concentrated agriculture system. Therefore, it has been required to find a safety economical nematocide which can be easily applied.

The known nematocides are mainly halogenohydrocarbon fumigants such as chloropicrin, methyl bromide, D-D(1,3-dichloropropene), EDB(ethylene dibromide), DCIP(bischloroisopropyl ether) and DBCP(1,2-dibromo-3-chloropropane) etc.

These nematocides are not easily used in view of a mucous stimulation and a metal corrosion. Although phytotoxicity is not found by using DBCP and DCIP, serious phytotoxicity is caused by using the other nematocides. Most of the nematocides are used in liquid forms, and accordingly, it is necessary to provide a water-seal of a soil surface for a while or to cover with a polyethylene film in order to impart the nematocidal effect and it is also necessary to discharge the nematocide in the atmosphere by a cultivation for a gas discharge after the treatment in the soil treatment. Thus, remarkable inconvenience is caused in the processing. DBCP can be granulated, however, the production of DBCP is inhibited in view of toxicity to human-body and a long residue of DBCP in a soil and underground water. DCIP has a low nematocidal effect.

In USA, certain contact nematocides as organophosphorus agents such as Fensulfothion (O,O-diethyl-O-(4-methylsufynyl)phenylphosphorothioate), Ethoprop(O-ethyl S,S-dipropylphosphorodithioate) and Phenamiphos[ethyl 3-methyl-4-(methylthio)phenyl(1-methylethyl)phosphoroamidate]; and carbamate agents such as Carbofuran (2,3-dihydro-2,2-dimethyl-7-benzofuranyl methyl carbamate), and Aldicarb[2-methyl-2-(methylthio)propionaldehyde O-(methylcarbomoyl)oxime] have been used.

These contact namatocides have remarkable toxicity and can be used in a form of granule only by a special expert.

The following nematode diseases have been known. Leaf nematode disease (*Aphelenchoides ritzema-bosi. Aphelenchoides fragariae*); Stem and bulb namatode disease (*Ditylenchus dipsaci*); Root knot nematode disease (*Meloidogyne incognita* var. *acrita*) and *Meloidogyne hapla*); Stem nematode disease (*Ditylenchus dipsaci*); Root lesion nematode disease (*Pratylenchus coffcae, Pratylenchus penetraus*); Cyst namatode disease (*Heterodera glycines* and *Globodera rostochiensis*).

SUMMARY OF THE INVENTION

It is an object of the present invention to provide a nematocide especially a soil nematocide which is safe and effective and can be easily applied.

The foregoing and other objects of the present invention have been attained by providing a nematocide especially a soil nematocide which comprises S-methyl-N,N-di-$C_{1-2}$ alkyl thiolcarbamate as an active ingredient.

DETAILED DESCRIPTION OF THE PREFERRED EMODIMENTS

The active ingredient can be S-methyl-N,N-dimethyl thiolcarbamate (b.p. 117° C./90 mmHg) or S-methyl-N,N-diethyl thiolcarbamate (b.p. 100° C./25 mmHg).

The compounds can be easily produced at a low cost by reacting methylthiochloroformate with dimethylamine or diethylamine and then reacting the resulting carbamate with methyl chloride or dimethyl sulfuric acid.

The active ingredient can be applied as a desired composition such as an emulsifiable concentrate, a wettable powder, a granule, a dust and an oil solution which is formed by mixing with suitable adjuvants in view of the application. The liquid or solid carrier or a combination thereof can be used.

Suitable solid carriers include bentonite, talc, kaolin, zeolite, clay and diatomaceous earth. Suitable liquid carriers include inert organic solvents such as xylene, o-chlorotoluene, methyl naphthalene, isophorone and kerosen.

In the preparation of the composition, it is preferable to incorporate a surfactant for imparting emulsifiability, dispersibility and spreadability. The composition can be prepared by the known technology.

The content of the active ingredient is in a range of 5 to 40 wt.% in the form of a granule or a dust and 5 to 90 wt.% in the form of an oil solution, an emulsifiable concentrate, a wettable powder.

The content of the surfactant is in a range of 0.5 to 30 wt.% preferably 2 to 20 wt.%.

The active ingredient and the surfactant are diluted with the liquid or solid carrier.

The active ingredient of the present invention is not only used as a single active ingredient but also can be used by mixing another agricultural chemical such as herbicides, germicides and insecticides, other pesticides and fertilizers.

It is especially preferable to apply the active ingredient in the form of the granule or a fine granule. In the preparation, the active ingredient is absorbed or adsorbed on a carrier for granule which has high oil absorption such as diatomaceous earth and fine silica with water if necessary with the other adjuvants.

The following is a list of certain compositions.

TABLE 1

| Active ingredient | Granule | | | | | | | | | | | | | | | |
|---|---|---|---|---|---|---|---|---|---|---|---|---|---|---|---|---|
| | 5 | | 10 | | 15 | | 20 | | 25 | | 30 | | 35 | | 40 | |
| Solid carrier | 93 | — | 88 | — | 83 | — | 78 | — | 73 | — | 68 | — | 63 | — | 58 | — |
| Liquid carrier | — | 93 | — | 88 | — | 83 | — | 78 | — | 73 | — | 68 | — | 63 | — | 58 |
| Surfactant | 2 | 2 | 2 | 2 | 2 | 2 | 2 | 2 | 2 | 2 | 2 | 2 | 2 | 2 | 2 | 2 |

EXAMPLE 1

Granule:

| S—methyl-N,N—diethylthiolcarbamate | 10 wt. parts |
|---|---|
| Granular diatomaceous earth | 90 wt. parts |

The active ingredient was immersed in the granular diatomaceous earth to obtain a granule.

EXAMPLE 2

Granule:

| S—methyl-N,N—diethylthiolcarbamate | 15 wt. parts |
|---|---|
| Fine silica (Carplex: Shionogi) | 15 wt. parts |
| Bentonite (Na Salt) | 65 wt. parts |
| Nonionic surfactant (Surfinol TGE: Air Prod. and Chem.) | 2 wt. parts |
| Dispersant (Lapizol B-80: Nippon Oil & Fat) | 3 wt. parts |

The components were mixed and ground and 15 wt. parts of was added and the mixture was kneaded and granulated and dried to obtain a granule.

EXAMPLE 3

Oil solution:

| S—methyl-N,N—diethylthiolcarbamate | 10 wt. parts |
|---|---|
| o-Chlorotoluene | 90 wt. parts |

The active ingredient was dissolved to obtain an oil solution.

EXAMPLE 4

Emulsifiable concentrate:

| S—methyl-N,N—diethylthiolcarbamate | 80 wt. parts |
|---|---|
| Xylene | 10 wt. parts |
| Nonionic surfactant (Sorpol 800A: Toho Chem.) | 10 wt. parts |

The active ingredient was dissolved to obtain an emulsifiable concentrate.

EXAMPLE 5

Granule:

| S—methyl-N,N—dimethylthiolcarbamate | 25 wt. parts |
|---|---|
| Granular diatomaceous earth | 75 wt. parts |

The active ingredient was immersed in the granular diatomaceous earth to obtain a granule.

EXAMPLE 6

Granule:

| S—methyl-N,N—dimethylthiolcarbamate | 25 wt. parts |
|---|---|
| Dispersing agent (surfactant) (Newcol 565 Nippon Emulsifier) | 5 wt. parts |
| Granular diatomaceous earth | 70 wt. parts |

A mixture of the active ingredient and the surfactant was immersed into the granular diatomaceous earth to obtain a granule.

EXAMPLE 7

Granule:

| S—methyl-N,N—diethylthiolcarbamate | 10 wt. parts |
|---|---|
| Granular zeolite | 90 wt. parts |

The active ingredient was immersed in the granular zeolite to obtain a granule.

EXAMPLE 8

Granule:

| S—methyl-N,N—dimethylthiolcarbamate | 15 wt. parts |
|---|---|
| Butyl carbitol | 15 wt. parts |
| Calcined granular diatomaceous earth | 70 wt. parts |

A mixture of the active ingredient and butyl carbitol was immersed in the sintered granular diatomaceous earth to obtain a granule.

EXAMPLE 9

Granule:

| S—methyl-N,N—diethylthiolcarbamate | 15 wt. parts |
|---|---|
| Dipropylene glycol | 15 wt. parts |
| Calcined granular diatomaceous earth | 70 wt. parts |

A mixture of the active ingredient and dipropyleneglycol was immersed in the calcined granular diatomaceous earrh to obtain a granule.

EXAMPLE 10

Granule:

| S—methyl-N,N—dimethylthiolcarbamate | 10 wt. parts |
|---|---|
| Castor oil | 10 wt. parts |
| Granular zeolite | 80 wt. parts |

A mixture of the active ingredient and castor oil was immersed in a granular zeolite to obtain a granule.

EXAMPLE 11

Granule:

| Bentonite (Na salt) | 45 wt. parts |
|---|---|
| Uncalcined diatomaceous earth | 54.5 wt. parts |

-continued

| | |
|---|---|
| Nonionic surfactant (Rapisol Nippon Oil & Fat) | 0.5 wt. parts |

These components were mixed with water and treated by a wet granulation and dried to obtain a granular carrier. In 90 wt. parts of the carrier, 10 wt. parts of S-methyl-N,N-diethylthiolcarbamate was immersed to obtain a granule.

EXAMPLE 12

Granule:

| | |
|---|---|
| Bentonite (Ca salt) | 80 wt. parts |
| Uncalcined diatomaceous earth | 20 wt. parts |

A mixture was mixed and ground and kneaded with water and granulated and dried to obtain a granular carrier. In 85 wt. parts of the active ingredient, 15 wt. parts of S-methyl-N,N-dimethylthiolcarbamate was immersed to obtain a granule.

EXAMPLE 13

Granule:

| | |
|---|---|
| Bentonite (Ca salt) neutralized with phosphoric acid | 90 wt. parts |
| S—methyl-N,N—diethylthiolcarbamate | 10 wt. parts |

The bentonite (Ca salt) neutralized with phosphoric acid (pH=7 in a concentration of 2 g/100 g of water) was kneaded with water and was granulated by a wet granulation and dried to obtain a granular carrier. In the carrier, S-methyl-N,N-diethylthiolcarbamate was immersed to obtain a granule.

EXAMPLE 14

Granule:

| | |
|---|---|
| Bentonite (Ca salt) | 68 wt. parts |
| Uncalcined diatomaceous earth | 30 wt. parts |
| Vinyl acetate emulsion (non-volatile matter) | 2 wt. parts |

The components were mixed and ground and kneaded with water and granulated by a wet granulation and dried to obtain a carrier. In 85 wt. parts of the carrier, 15 wt. parts of S-methyl-N,N-dimethylthiolcarbamate was immersed to obtain a granulate.

EXAMPLE 15

Aqueous solution:
In water 10 wt. parts of S-methyl-N,N-dimethylthiolcarbamate was dissolved to obtain an aqueous solution.

EXAMPLE 16

Granule:

| | |
|---|---|
| S—methyl-N,N—dimethyldithiocarbamate | 25 wt. parts |
| Pyrophylite (Fubasamiclay: Onuki Kozan) | 50 wt. parts |
| Fine silica (Carplex: Shionogi) | 25 wt. parts |

The active ingredient was adsorbed on fine silica and pyrophylite was mixed to obtain a granule.

EXAMPLE 17

Emulsifiable concentrate:

| | |
|---|---|
| S—methyl-N,N—dimethyldithiocarbamate | 10 wt. parts |
| Xylene | 85 wt. parts |
| Nonionic surfactant (Sorpol 800A: Toho Chemical) | 5 wt. parts |

The active ingredient was mixed with xylene and the nonionic surfactant to obtain an emulsifiable concentrate.

The effects of the nematocide compositions of the present invention will be illustrated by certain experimental tests.

TEST 1

Test for controlling *meloidogyne incognita* in tomato

A soil infected by *meloidogyne incognita* multiplicated on sweet potato as a host plant was filled in a 1/10000 a pot having a height of 14 cm. Each granule prepared in accordance with the composition of Example 1 was mixed at a predetermined ratio. As a reference, the commercially available nematocidal compositions; 30% DCIP granule or 20% DBCP. Granule was also mixed. Seven days after the treatment, 10 seeds of tomato were sowed in each pot.

The test was performed in a glass greenhouse at 25° to 30° C. One month after the sowing, each degree of root knot caused by parasitism, each phytotoxicity and each weight of stem and leaf were measured. The tests were repeated for 3 times. Average data are shown in Table 2.

The same tests were performed by using the active ingredient in various forms of compositions such as those of Example No. 5, No. 16 and No. 17. The results are shown in Table 2.

The degree of root knot caused by parasitism and the phytotoxicity were shown by the following rating.

| Degree of root knot | Percent Infection | Number of root knots |
|---|---|---|
| 0 | 0 | none |
| 1 | 1–25% | 1–8 |
| 2 | 25–50% | 9–20 |
| 3 | 51–75% | 21–30 |
| 4 | 76–100% | >30 |

Phytotoxicity
− none
± slight damage
+ damage
++ serious damage
+++ death without germination

TABLE 1

| Composition | Dosage of formulated product (kg/10 a) | Degree of root knot | Weight of stem leaf (g/seedling) | Phytotoxicity |
|---|---|---|---|---|
| O‖ (C$_2$H$_5$)$_2$NCSCH$_3$ 10% granule | 4 | 0.00 | 0.87 | − |
| | 2 | 0.21 | 0.81 | − |
| | 1 | 0.92 | 0.90 | − |
| O‖ (CH$_3$)$_2$NCSCH$_3$ 10% granule | 4 | 0.12 | 0.84 | − |
| | 2 | 1.31 | 0.88 | − |
| | 1 | 2.75 | 0.67 | − |

TABLE 1-continued

| Composition | Dosage of formulated product (kg/10 a) | Degree of root knot | Weight of stem leaf (g/seedling) | Phytotoxicity |
|---|---|---|---|---|
| $(CH_3)_2NCSC_2H_5$ 10% granule | 4 | 1.14 | 0.84 | +[*1] |
|  | 2 | 2.56 | 0.65 | ±[*1] |
| $(CH_3)_2NCSC_4H_9$ 10% granule | 4 | 1.63 | 0.71 | ++[*2] |
|  | 2 | 3.00 | 0.49 | +[*1] |
| $(C_2H_5)_2NCSC_2H_5$ 10% granule | 4 | 2.47 | 0.29 | +++[*3] |
|  | 2 | 3.83 | 0.32 | ++[*2] |
| DBCP 20% granule | 4 | 0.29 | 0.73 | ± |
| DCIP 30% granule | 9 | 3.32 | 0.42 | — |
| Non-treatment | — | 3.93 | 0.18 | — |

[*1] Stem discoloring
[*2] Leaf edge drying
[*3] Leaf drying, stem discoloring

TABLE 2'

| Composition | Dosage of formulated product (kg/10 a) | Degree of root knot | Weight of stem leaf (g/seedling) | Phytotoxicity |
|---|---|---|---|---|
| $(CH_3)_2NCSCH_3$ 25% granule | 20 | 0.00 | 0.99 | — |
|  | 10 | 0.98 | 1.01 | — |
| $(CH_3)_2NCSCH_3$ 25% dust | 20 | 1.62 | 0.95 | — |
|  | 10 | 3.33 | 0.66 | — |
| $(CH_3)_2NCSCH_3$ 10% emul. conc. | 20 times dil. 1000 l/10 a | 2.87 | 0.51 | — |
|  | 40 times dil. 1000 l/10 a | 3.54 | 0.34 | — |
| $(CH_3)_2NCSC_2H_5$ 25% granule | 20 | 0.89 | 0.94 | +[*1] |
|  | 10 | 2.17 | 0.70 | ±[*1] |
| $(CH_3)_2NCSC_3H_7$ 25% granule | 20 | 1.25 | 0.85 | ++[*2] |
|  | 10 | 2.15 | 0.63 | +[*1] |
| $(CH_3)_2NCSC_4H_9$ 25% granule | 20 | 1.99 | 0.67 | ++[*2] |
|  | 10 | 2.83 | 0.46 | +[*1] |
| $(CH_3)_2NCSC_4H_9$ 25% dust | 20 | 3.22 | 0.58 | +[*2] |
|  | 10 | 3.84 | 0.27 | +[*1] |
| $(CH_3)_2NCSC_4H_9$ 10% emul. conc. | 20 times dil. 1000 l/10 a | 3.21 | 0.42 | +[*1] |
|  | 40 times dil. 1000 l/10 a | 3.86 | 0.12 | ±[*1] |
| $(C_2H_5)_2NCSC_2H_5$ 25% granule | 20 | 2.19 | 0.28 | +++[*3] |
|  | 10 | 3.52 | 0.30 | ++[*2] |
| DBCP 20% granule | 20 | 0.50 | 0.75 | ± |
| DCIP 30% granule | 30 | 3.32 | 0.46 | — |
| Non-treatment | — | 4.00 | 0.08 | — |

TEST 2

Test for controlling *meloidogyne incognite* in tomato by oil solution and emulsifiable concentrate of invention Each oil solution prepared in accordance with the composition of Example 3 or each emulsifiable concentrate prepared in accordance with the composition of Example 4 to contain each predetermined content of the active ingredient was diluted with water to 4 times, 8 times or 16 times and each diluted solution was poured at a center in a depth of 8 cm in each at a rate of 15 liter/10 a or 20 liter/10 a. Then, each pot was sealed with 50 ml. of water.

As a reference, the commercially available D-D, and EDB were also applied in the same manner. Five days after the treatment, the soil was cultivated for the gas discharge. Eight days after the treatment with the composition, seeds of tomato were sowed as Test 1. One month after the sowing, each degree of root knot caused by parasitism and phytotoxicity were measured. The results (average) are shown in Table 3.

TABLE 3

| Composition | Dosage of formulated product (kg/10 a) | Degree of root knot | Weight of stem leaf (g/seedling) | Phytotoxicity |
|---|---|---|---|---|
| $(C_2H_5)_2NCSCH_3$ 10% oil sol. | 3 | 0.64 | 1.10 | — |
|  | 2 | 1.06 | 0.82 | — |
|  | 1 | 1.39 | 0.94 | — |
| $(C_2H_5)_2NCSCH_3$ 80% emul. conc. dilution | 3 | 0.50 | 0.88 | — |
|  | 2 | 1.12 | 1.03 | — |
|  | 1 | 1.53 | 0.86 | — |
| D—D 55% oil sol. | 16.5 | 1.43 | 0.85 | — |
| EDB 30% oil sol. | 9 | 1.32 | 0.88 | — |
| Non-treatment | — | 3.93 | 0.18 | — |

TEST 3

Test for controlling *pratylenchus penetrans* in burdock by granule of invention A soil infected by *pratylenchus penetrans* multiplicated on kidney bean as a host plant was filled in a 1/10000 a pot having a height of 14 cm. Each granule prepared in accordance with the Example 2 was mixed at a predetermined ratio. As a reference, the commercially available nematocidal compositions. Seven days after the treatment, 5 seeds of burdock were sowed in each pot. The test was performed in a glass greenhouse at 25° to 30° C. Fifty days after the sowing, each degree of root damage caused by parasitism, each phytotoxicity and each weight were measured. The results are shown in Table 4. The degree of root damage was tested as the rating in Test 1.

| Degree of root damage | Number of brown colored lesions | Percent infection |
|---|---|---|
| 0 | 0 | 0 |
| 1 | 1-5 | 1-25% |
| 2 | 6-10 | 26-50% |
| 3 | 11-15 | 51-75% |
| 4 | >16 | 76-100% |

The same tests were performed by using the active ingredient in various forms of compositions such as those of Example No. 5 and No. 16. The results are shown in Table 4'.

TABLE 4

| Composition | Dosage of formulated product (kg/10 a) | Degree of root damage | Total weight (g/piece) | Phyto-toxicity |
|---|---|---|---|---|
| $(C_2H_5)_2NCSCH_3$ 15% granule | 6 | 0.89 | 2.62 | — |
|  | 3 | 1.78 | 2.25 | — |
| $(CH_3)_2NCSCH_3$ 15% granule | 6 | 1.63 | 2.46 | — |
|  | 3 | 2.36 | 2.03 | — |
| $(CH_3)_2NCSC_2H_5$ 15% granule | 6 | 2.14 | 1.81 | + |
|  | 3 | 3.14 | 1.77 | ± |
| $(CH_3)_2NCSC_4H_9$ 15% granule | 6 | 2.59 | 1.73 | + |
|  | 3 | 3.25 | 1.75 | ± |
| DBCP 20% granule | 6 | 1.46 | 2.48 | — |
| Non-treatment | — | 3.31 | 1.80 | — |

TABLE 4'

| Composition | Dosage of formulated product (kg/10 a) | Degree of root knot | Total weight (g/piece) | Phyto-toxicity |
|---|---|---|---|---|
| $(CH_3)_2NCSCH_3$ 25% granule | 30 | 0.83 | 2.41 | — |
|  | 20 | 1.61 | 2.31 | — |
| $(CH_3)_2NCSC_4H_9$ 25% granule | 30 | 2.05 | 1.81 | + |
|  | 20 | 2.74 | 1.96 | ± |
| $(CH_3)_2NCSCH_3$ 25% dust | 30 | 1.87 | 2.24 | — |
|  | 20 | 2.80 | 1.83 | — |
| DBCP 20% granule | 30 | 1.39 | 2.36 | — |
| Non-treatment | — | 3.20 | 1.70 | — |

TEST 4

Test for controlling *meloidogyne incognita* in cucumber in paddy field

On a paddy field infected by *meloidogyne incognita* in the preceding cropping of a sweet potato, a predetermined amount of each granule prepared in accordance with the process of Example 1 was sprayed on all surface and the soil was cultivated to mix the granule. The reference compositions were also applied in the same manner. Five days after the treatment, 16 cucumber seedlings at 5 leaf stage were transplanted in each section of 4 m². The test was repeated twice. The irrigation and the pesticidal treatment were perforemed. The tests were performed from June 16 to August 14th. On August 14th, each degree of root knot caused by parasitism each phytotoxicity and length of cucumber including branches were measured in accordance with Test 1. The results (average) are shown in Table 5.

TABLE 5

| Composition | Dosage of formulated product (kg/10 a) | Degree of parasitism | Length of cucumber (cm/seedling) | Phyto-toxicity |
|---|---|---|---|---|
| $(C_2H_5)_2NCSCH_3$ 10% granule | 2 | 0.92 | 315 | — |
|  | 3 | 0.50 | 308 | — |
| $(CH_3)_2NCSCH_3$ 10% granule | 2 | 2.83 | 231 | — |
|  | 3 | 1.83 | 299 | — |
| DBCP 20% granule | 4 | 1.19 | 312 | — |
| Non-treatment | — | 3.10 | 194 | — |

TABLE 5'

| Composition | Dosage of formulated product (kg/10 a) | Degree of parasitism | Length of cucumber (cm/seedling) | Phyto-toxicity |
|---|---|---|---|---|
| $(CH_3)_2NCSCH_3$ 25% granule | 30 | 0.13 | 291 | — |
|  | 20 | 0.64 | 303 | — |
| $(CH_3)_2NCSC_4H_9$ 25% granule | 30 | 2.22 | 219 | ± |
|  | 20 | 2.86 | 234 | — |
| $(CH_3)_2NCSCH_3$ 25% dust | 30 | 1.18 | 280 | — |
|  | 20 | 1.99 | 262 | — |
| DBCP 20% granule | 20 | 0.75 | 297 | — |
| Non-treatment | — | 3.45 | 205 | — |

As shown in Tests, S-methyl- or ethyl-N,N-diethyl-thiolcarbamate imparts remarkably high effects for controlling *meloidogyne incognite* and *pratylenchus penetrans* which cause serious damages to crops. Moreover, the active ingredient does not cause phytotoxicity to tomato, cucumber and burdock.

What is claimed is:

1. A formulation for a parasitic-nematocidal composition comprising 5-40% of S-methyl-N,N-di $C_{1-2}$ alkyl-thiocarbamate as an active ingredient of said composition; and an inert carrier; wherein the improvement comprises:

formulating said nematocidal composition in the form of granules.

2. The formulation according to claim 1, wherein said carrier is silica, bentonite, pyrophylite, talc, kaolin, zeolite, clay or diatomaceous earth.

3. The formulation according to claim 1, wherein said composition further comprises 0.5 to 30 wt. % of a surfactant.

4. The formulation according to claim 1, wherein said active ingredient is S-methyl-N,N-dimethylthiolcarbamate.

5. The formulation according to claim 1, wherein said active ingredient is S-methyl-N,N-diethylthiolcarbamate.

6. The formulation of claim 4, wherein the amount of S-methyl-N,N-dimethylthiolcarbamate is between about 15 and 25% of said composition.

7. The formulation of claim 5, wherein the amount of S-methyl-N,N-diethylthiolcarbamate is 10% or more of said composition.

* * * * *